United States Patent
Yang et al.

(10) Patent No.: US 12,310,718 B2
(45) Date of Patent: May 27, 2025

(54) MILLIMETER-WAVE (mmWAVE) RADAR-BASED NON-CONTACT IDENTITY RECOGNITION METHOD AND SYSTEM

(71) Applicant: CENTRAL CHINA NORMAL UNIVERSITY, Hubei (CN)

(72) Inventors: Zongkai Yang, Hubei (CN); Sannyuya Liu, Hubei (CN); Liang Zhao, Hubei (CN); Zhicheng Dai, Hubei (CN); Jianwen Sun, Hubei (CN); Qing Li, Hubei (CN)

(73) Assignee: CENTRAL CHINA NORMAL UNIVERSITY, Hubei (CN)

( * ) Notice: Subject to any disclaimer, the term of this patent is extended or adjusted under 35 U.S.C. 154(b) by 137 days.

(21) Appl. No.: 18/038,213

(22) PCT Filed: Apr. 22, 2021

(86) PCT No.: PCT/CN2021/088947
§ 371 (c)(1),
(2) Date: May 23, 2023

(87) PCT Pub. No.: WO2022/116467
PCT Pub. Date: Jun. 9, 2022

(65) Prior Publication Data
US 2024/0000345 A1 Jan. 4, 2024

(30) Foreign Application Priority Data
Dec. 3, 2020 (CN) .......................... 202011393333.7

(51) Int. Cl.
*A61B 5/117* (2016.01)
*A61B 5/024* (2006.01)
(Continued)

(52) U.S. Cl.
CPC .............. *A61B 5/117* (2013.01); *A61B 5/024* (2013.01); *G01S 13/88* (2013.01); *G06F 18/20* (2023.01)

(58) Field of Classification Search
CPC ....... A61B 5/024; A61B 5/0507; A61B 5/117; G01S 13/88; G01S 7/354; G01S 7/414;
(Continued)

(56) References Cited

U.S. PATENT DOCUMENTS

2014/0148709 A1  5/2014  Gu et al.
2019/0094350 A1*  3/2019  Baheti ..................... G01S 7/415

FOREIGN PATENT DOCUMENTS

CN  106485213  3/2017
CN  108537100  9/2018
(Continued)

OTHER PUBLICATIONS

"International Search Report (Form PCT/ISA/210) of PCT/CN2021/088947", mailed on Aug. 26, 2021, with English translation thereof, pp. 1-4.
(Continued)

*Primary Examiner* — Michael T Rozanski
(74) *Attorney, Agent, or Firm* — JCIPRNET

(57) ABSTRACT

Disclosed are a millimeter-wave (mmWave) radar-based non-contact identity recognition method and system. The method comprises: emitting an mmWave radar signal to a user to be recognized, and receiving an echo signal reflected from the user; performing clutter suppression and echo selection on the echo signal, and extracting a heartbeat signal; segmenting the heartbeat signal beat by beat, and determining its corresponding beat features; and comparing the beat features of the user with the beat feature sets of a standard user group; if the beat features of the user matches one of the beat feature set of in the standard user group, the
(Continued)

identity recognition being successful; otherwise, being not successful. According to the method, the use of a heartbeat signal for identity recognition has high reliability, and the use of an mmWave radar technology for non-contact identity recognition has high flexibility and accuracy.

7 Claims, 6 Drawing Sheets

(51) Int. Cl.
 *G01S 13/88* (2006.01)
 *G06F 18/20* (2023.01)
(58) Field of Classification Search
 CPC .......... G01S 7/415; G01S 7/417; G06F 18/20; G06N 3/04
 See application file for complete search history.

(56) References Cited

FOREIGN PATENT DOCUMENTS

| | | |
|---|---|---|
| CN | 110475153 | 11/2019 |
| CN | 111398944 | 7/2020 |
| CN | 112686094 | 4/2021 |

OTHER PUBLICATIONS

"Written Opinion of the International Searching Authority (Form PCT/ISA/237) of PCT/CN2021/088947", mailed on Aug. 26, 2021, pp. 1-5.

\* cited by examiner

MILLIMETER-WAVE (mmWAVE) RADAR-BASED NON-CONTACT IDENTITY RECOGNITION METHOD AND SYSTEM

CROSS-REFERENCE TO RELATED APPLICATION

This application is a 371 of international application of PCT application serial no. PCT/CN2021/088947, filed on Apr. 22, 2021, which claims the priority benefit of China application serial no. 202011393333.7, filed on Dec. 3, 2020. The entirety of each of the above-mentioned patent applications is hereby incorporated by reference herein and made a part of this specification.

BACKGROUND

Technical Field

The disclosure belongs to cross-border development of radar and biological feature recognition, and more specifically relates to a millimetre-wave (mmWave) radar-based non-contact identity recognition method and system.

Description of Related Art

Data is present in every aspect of life as technologies continue to develop. It is urgent to find out how to innovate identification technology in the era of big data, effectively protect user privacy and improve user experience while improving security protection.

Conventional identification is performed by mainly relying on "account+password" and the like, and such methods have low protection level and lack convenience. In contrast, with flexibility and diversity and other advantages, biometric identification technology has gradually emerged in recent years and has been widely adopted. Common biometric identification technologies include: face recognition, voice recognition, fingerprint recognition, etc. Compared with conventional technologies, although the protection level of biometric identification has been significantly improved, the problem of existing technologies such as: face recognition, voice recognition, fingerprint recognition, etc. lies in that face, voice and fingerprint are likely to be imitated and deciphered, and therefore security issues are yet to be overcome.

SUMMARY

To solve the defects of related art, the purpose of the present disclosure is to provide an mmWave radar-based non-contact identity recognition method and system, which seek to solve the security issues of existing biometric identification technology for being easily imitated and deciphered.

In order to achieve the above purpose, the first aspect of the present disclosure provides an mmWave radar-based non-contact identity recognition method, which includes the following steps: transmitting an mmWave radar signal to a user to be recognized, and receiving an echo signal reflected from the user to be recognized; performing clutter suppression and echo selection on the echo signal, and then extracting a heartbeat signal of the user to be recognized; segmenting the heartbeat signal of the user to be recognized beat by beat, and determining its corresponding beat features of the user to be recognized; and comparing the beat features of the user to be recognized with the beat feature sets of a standard user group; if the beat features of the user to be recognized matches a beat feature set of one standard user in the standard user group, the identity recognition for the user to be recognized is successful; otherwise, the identity recognition for the user to be recognized is not successful.

Specifically, transmitting an mmWave radar signal to a user may be carried out through, for example, an mmWave transceiver module, and the mmWave transceiver module does not need to be in direct contact with the user, so it is possible to realize non-contact identification.

In an optional embodiment, the heartbeat signal of the user to be recognized is segmented beat by beat. If only a single-beat signal is included after the segmentation, the time-frequency domain features corresponding to the single-beat signal are determined as the beat features of the user to be recognized; if a multiple-beat signal is included after the segmentation, the time-frequency domain features of each beat signal are determined separately, and the time-frequency domain features are input into the neural network to extract its corresponding time-series features, so that the time-frequency domain features and time-series features are used as the beat features of the user to be recognized.

In an optional embodiment, performing echo selection on the echo signal specifically includes the following: performing Fourier transform on each row of the echo signal to obtain the range-time map matrix of the mmWave radar; calculating the sum of energy on the distance unit characterized by each column of the range-time map matrix, and selecting the maximum energy and the corresponding distance unit as the distance from the mmWave radar transmitting point to the user to be recognized, and extracting the maximum energy and the corresponding column in the range-time map matrix, utilizing the arctangent function to calculate the phase of the column and performing a phase unwrapping operation to obtain the signal related to the vital sign of the user to be recognized in the echo signal.

In an optional embodiment, extracting the heartbeat signal of the user to be recognized after performing echo selection specifically includes the following: performing discrete wavelet transform on the signal subjected to the phase unwrapping operation, and performing bandpass filtering on the signal subjected to discrete wavelet transform; performing inverse wavelet transform on the signal subjected to bandpass filtering to reconstruct the heartbeat signal of the user to be recognized.

In an optional embodiment, segmenting the heartbeat signal of the user to be recognized into the beat signal specifically includes the following: after turning the heartbeat signal of the user to be recognized upside down by 180°, utilizing peak detection to identify the valley, and the peak value and peak-to-peak distance thereof are greater than the preset threshold; then turning the heartbeat signal back and determining whether there is a valid peak between two valleys; the valid peak should meet the following two conditions simultaneously: (i) the peak value exceeds the preset peak value threshold; (ii) there is a zero-crossing point (which is identified by zero-crossing detection) between two valleys; if there is a valid peak, the beat segmentation is performed according to the front and rear valleys; if there is no valid peak, the beat segmentation is not performed.

In an optional embodiment, comparing the beat features of the user to be recognized with the beat feature sets of a standard user group specifically include the following: if the heartbeat signal of the user to be recognized contains only a single-beat signal after segmentation, the beat feature sets of the standard user group are extracted one by one, and a first classifier is utilized to identify the time-frequency domain features of the single-beat signal of the user to be recognized, the recognition result is a vector w, w=[$p_1$, $p_2$, ..., $p_m$], and the element $p_j$ in the vector w represents the probability that the beat of the user to be recognized is the j-th standard user in the standard user group, j∈[1, m], m represents that there are m users in the standard user group; if the maximum value of elements in the vector w is greater than the preset probability threshold, the identity recognition for the user to be recognized is successful, and the user's identity is determined to be the standard user corresponding to the maximum value of elements in the vector w; if the heartbeat signal of the user to be recognized contains multiple-beat signals after segmentation, the beat feature sets of the standard user group are extracted one by one, first of all, the first classifier is utilized to identify the time-frequency domain features of the multiple-beat signals of the user to be recognized, the recognition result is a matrix W of n×m dimensions, $$W = \begin{bmatrix} p_{11} & \cdots & p_{1m} \\ \vdots & p_{ij} & \vdots \\ p_{n1} & \cdots & p_{nm} \end{bmatrix},$$

i∈[1, n], j∈[1, m], n represents that the user to be recognized contains n beat signals after segmentation, m represents that there are m users in the standard user group, and the element $p_{ij}$ in the matrix w represents the probability that the i-th beat of the user to be recognized is the j-th standard user in the standard user group, the average function is adopted to average each column of the probability matrix W to obtain a vector $\bar{w}$, $\bar{w}$=[$\bar{p}_1$, $\bar{p}_2$, ... $\bar{p}_m$], j∈[1, m]; the element $\bar{p}_j$ in the vector $\bar{w}$ represents the average probability that the multiple-beat recognition result of the user to be recognized is the j-th standard user in the standard user group; if the maximum value of elements in the vector $\bar{w}$ is greater than the preset probability threshold, it is preliminarily determined that the user's identity is the standard user corresponding to the maximum value of elements in the vector $\bar{w}$. Next, the vector $\bar{w}$ identified by the first classifier is fused with the time-series domain features of the multiple-beat signals of the user to be recognized, a second classifier is adopted to perform identity recognition based on the fused features, and finally it is determined whether the identity recognition for the user to be recognized is successful, if the identity recognition is successful, the user is further determined as the standard user with corresponding identity.

The second aspect of the present disclosure provides an mmWave radar-based non-contact identity recognition system, which includes: a signal transmitting unit, transmitting an mmWave radar signal to a user to be recognized; a signal receiving unit, receiving the echo signal reflected from the user to be recognized; a heartbeat signal extracting unit, performing clutter suppression and echo selection on the echo signal and extracting the heartbeat signal of the user to be recognized; a beat feature determining unit, segmenting the heartbeat signal of the user to be recognized beat by beat, and determining the corresponding beat features of the user to be recognized; and an identity recognizing unit, comparing the beat features of the user to be recognized with the beat feature sets of a standard user group; if the beat features of the user to be recognized matches a beat feature set of one standard user in the standard user group, the identity recognition for the user to be recognized is successful; otherwise, the identity recognition for the user to be recognized is not successful.

Specifically, the signal transmitting unit and the signal receiving unit may be composed into an mmWave transceiver module.

In an optional embodiment, the beat feature determining unit segments the heartbeat signal of the user to be recognized beat by beat. If only a single-beat signal is included after the segmentation, the time-frequency domain features corresponding to the single-beat signal are determined as the beat features of the user to be recognized; if multiple-beat signals are included after the segmentation, the time-frequency domain features of each beat signal are determined separately, and then the time-frequency domain features are input into the neural network to extract its corresponding time-series features, so that the time-frequency domain features and time-series features are used as the beat features of the user to be recognized.

In an optional embodiment, the heartbeat signal extracting unit performs Fourier transform on each row of the echo signal to obtain the range-time map matrix of the mmWave radar; calculates the sum of energy on the distance unit characterized by each column of the range-time map matrix, and selects the maximum energy and the corresponding distance unit as the distance from the mmWave radar transmitting point to the user to be recognized, and extracts the maximum energy and the corresponding column in the range-time map matrix, utilizes the arctangent function to calculate the phase of the column and performs a phase unwrapping operation to obtain the signal related to the vital sign of the user to be recognized in the echo signal.

In an optional embodiment, the heartbeat signal of the user to be recognized contains only a single-beat signal after segmentation, the identity recognizing unit extracts the beat feature sets of the standard user group one by one, and utilizes the first classifier to identify the time-frequency domain features of the single-beat signal of the user to be recognized, the recognition result is a vector w, w [$p_1$, $p_2$, ..., $p_m$], and the element $p_j$ in the vector w represents the probability that the beat of the user to be recognized is the j-th standard user in the standard user group, j∈[1, m], m represents that there are m users in the standard user group; if the maximum value of elements in the vector w is greater than the preset probability threshold, the identity recognition for the user to be recognized is successful, and the user's identity is determined to be the standard user corresponding to the maximum value of elements in the vector w; if the heartbeat signal of the user to be recognized contains multiple-beat signals after segmentation, the identity recognizing unit extracts the beat feature sets of the standard user group one by one, first of all, the first classifier is utilized to identify the time-frequency domain features of the multiple-beat signals of the user to be recognized, the recognition result is a matrix W of n×m dimensions, $$W = \begin{bmatrix} p_{11} & \cdots & p_{1m} \\ \vdots & p_{ij} & \vdots \\ p_{n1} & \cdots & p_{nm} \end{bmatrix},$$

i∈[1, n], j∈[1, m], n represents that the user to be recognized contains n beats after segmentation, m represents that there are m users in the standard user group, and the element $p_{ij}$ in the matrix w represents the probability that the i-th beat of the user to be recognized is the j-th standard user in the standard user group, the average function is adopted to average each column of the probability matrix W to obtain a vector $\bar{w}$, $\bar{w}=[\bar{p}_1, \bar{p}_2, \ldots, \bar{p}_m]$, $j\in[1, m]$; the element $\bar{p}_j$ in the vector $\bar{w}$ represents the average probability that the multiple-beat recognition result of the user to be recognized is the j-th standard user in the standard user group; if the maximum value of elements in the vector $\bar{w}$ is greater than the preset probability threshold, it is preliminarily determined that the user's identity is the standard user corresponding to the maximum value of elements in the vector $\bar{w}$. Next, the vector $\bar{w}$ identified by the first classifier is fused with the time-series domain features of the multiple-beat signals of the user to be recognized, the second classifier is adopted to perform identity recognition based on the fused features, and finally it is determined whether the identity recognition for the user to be recognized is successful, if the identity recognition is successful, the user is further determined as the standard user with corresponding identity.

Generally speaking, compared with the related art, the above technical solution conceived by the present disclosure has the following advantageous effects:

The present disclosure provides an mm Wave radar-based non-contact identity recognition method and system. On the one hand, the heartbeat signal is adopted for user identity recognition. As a biomedical signal, the heartbeat signal is characterized in singularity, uniqueness, and stability, and is not easy to be imitated. Using this signal for biometric identification may effectively improve the reliability of the recognition system. On the other hand, mmWave radar technology is adopted for non-contact identity recognition. MmWave technology is characterized in low power and high precision. Using such technology to sense heartbeat signals of human without having contact may effectively improve the flexibility and accuracy of the recognition system.

DESCRIPTION OF THE EMBODIMENTS

In order to make the purpose, technical solution and advantages of the present disclosure more comprehensible, the present disclosure will be further described in detail below in conjunction with the accompanying drawings and embodiments. It should be understood that the specific embodiments described here are only used to explain the present disclosure, not to limit the present disclosure.

To solve the problem indicated above, the present disclosure innovatively provides an mmWave radar-based non-contact identity recognition system and method, in which mmWave technology is introduced into the field of biometric identification to make full use of advantages of the two technologies. On the one hand, as a biomedical signal, the heartbeat signal is characterized in singularity, uniqueness, and stability, and is not easy to be imitated. Using this signal for biometric identification may effectively improve the reliability of the recognition system. On the other hand, mmWave radar technology is adopted for non-contact identity recognition. MmWave technology is characterized in low power and high precision. Using such technology to sense heartbeat signals of human without having contact may effectively improve the flexibility and accuracy of the recognition system.

Figure 1:
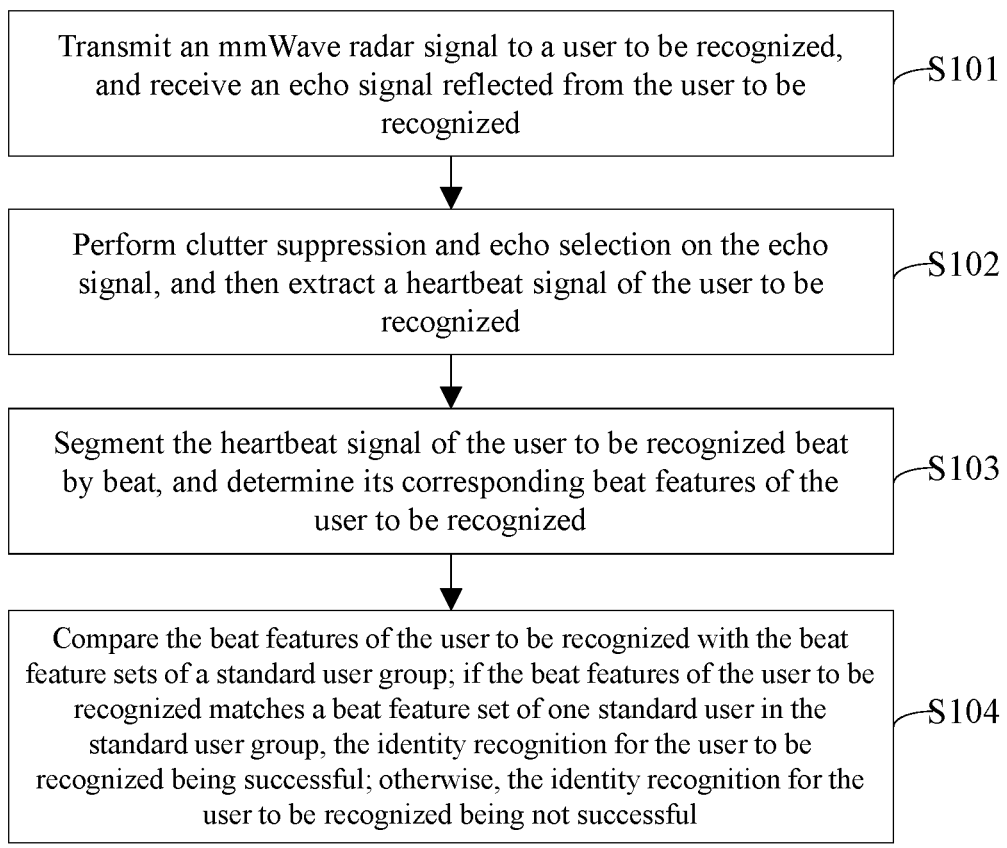
FIG. 1 is a flowchart of an mmWave radar-based non-contact identity recognition method provided by an embodiment of the present disclosure.

FIG. 1 is a flowchart of an mmWave radar-based non-contact identity recognition method provided by an embodiment of the present disclosure, as shown in FIG. 1, the method includes the following steps: S101, transmitting an mmWave radar signal to a user to be recognized, and receiving an echo signal reflected from the user to be recognized; S102, performing clutter suppression and echo selection on the echo signal, and then extracting a heartbeat signal of the user to be recognized; S103, segmenting the heartbeat signal of the user to be recognized beat by beat, and determining its corresponding beat features of the user to be recognized; and S104, comparing the beat feature sets of the user to be recognized with beat features of a standard user group; if the beat features of the user to be recognized matches a beat feature set of one standard user in the standard user group, the identity recognition for the user to be recognized is successful; otherwise, the identity recognition for the user to be recognized is not successful.

In an optional embodiment, the heartbeat signal of the user to be recognized is segmented beat by beat. If only a single-beat signal is included after the segmentation, the time-frequency domain features corresponding to the single-beat signal is determined as the beat features of the user to be recognized; if multiple-beat signals are included after the segmentation, the time-frequency domain features of each beat signal are determined separately, and the time-frequency domain features are input into the neural network to extract its corresponding time-series features, so that the time-frequency domain features and time-series features are used as the beat features of the user to be recognized.

In an optional embodiment, performing echo selection on the echo signal specifically includes the following: performing Fourier transform on each row of the echo signal to obtain the range-time map matrix of the mmWave radar; calculating the sum of energy on the distance unit characterized by each column of the range-time map matrix, and selecting the maximum energy and the corresponding distance unit as the distance from the mmWave radar transmitting point to the user to be recognized, and extracting the maximum energy and the corresponding column in the range-time map matrix, utilizing the arctangent function to calculate the phase of the column and performing a phase unwrapping operation to obtain the signal related to the vital sign of the user to be recognized in the echo signal.

In an optional embodiment, extracting the heartbeat signal of the user to be recognized after performing echo selection specifically includes the following: performing discrete wavelet transform on the signal subjected to the phase unwrapping operation, and performing bandpass filtering on the signal subjected to discrete wavelet transform; performing inverse wavelet transform on the signal subjected to bandpass filtering to reconstruct the heartbeat signal of the user to be recognized.

In an optional embodiment, segmenting the heartbeat signal of the user to be recognized into the beat signal specifically includes the following: after turning the heartbeat signal of the user to be recognized upside down by 180°, utilizing peak detection to identify the valley, and the peak value and peak-to-peak distance thereof are greater than the preset threshold; then turning the heartbeat signal back and determining whether there is a valid peak between two valleys; the valid peak should meet the following two conditions simultaneously: (i) the peak value exceeds the preset peak value threshold; (ii) there is a zero-crossing point (which is identified by zero-crossing detection) between two valleys; if there is a valid peak, the beat segmentation is performed according to the front and rear valleys; if there is no valid peak, the beat segmentation is not performed.

In an optional embodiment, comparing the beat features of the user to be recognized with the beat feature sets of a standard user group specifically includes the following: if the heartbeat signal of the user to be recognized contains only a single-beat signal after segmentation, the beat feature sets of the standard user group are extracted one by one, and the first classifier is utilized to identify the time-frequency domain features of the single-beat signal of the user to be recognized, the recognition result is a vector w, w=[$p_1$, $p_2$, . . . , $p_m$], and the element $p_j$ in the vector w represents the probability that the beat of the user to be recognized is the j-th standard user in the standard user group, j∈[1, m], m represents that there are m users in the standard user group; if the maximum value of elements in the vector w is greater than the preset probability threshold, the identity recognition for the user to be recognized is successful, and the user's identity is determined to be the standard user corresponding to the maximum value of elements in the vector w; if the heartbeat signal of the user to be recognized contains multiple-beat signals after segmentation, the beat feature sets of the standard user group are extracted one by one, first of all, the first classifier is utilized to identify the time-frequency domain features of the multiple-beat signals of the user to be recognized, the recognition result is a matrix W of n×m dimensions, $$W = \begin{bmatrix} p_{11} & \cdots & p_{1m} \\ \vdots & p_{ij} & \vdots \\ p_{n1} & \cdots & p_{nm} \end{bmatrix},$$

i∈[1, n], j∈[1, m], n represents that the user to be recognized contains n beats after segmentation, m represents that there are m users in the standard user group, and the element $p_{ij}$ in the matrix w represents the probability that the i-th beat of the user to be recognized is the j-th standard user in the standard user group, the average function is adopted to average each column of the probability matrix W to obtain a vector $\bar{w}$, $\bar{w}$=[$\bar{p}_1$, $\bar{p}_2$, . . . , $\bar{p}_m$], j∈[1, m]; the element $\bar{p}_j$ in the vector $\bar{w}$ represents the average probability that the multiple-beat recognition result of the user to be recognized is the j-th standard user in the standard user group; if the maximum value of elements in the vector $\bar{w}$ is greater than the preset probability threshold, it is preliminarily determined that the user's identity is the standard user corresponding to the maximum value of elements in the vector $\bar{w}$. Next, the vector $\bar{w}$ identified by the first classifier is fused with the time-series domain features of the multiple-beat signals of the user to be recognized, the second classifier is adopted to perform identity recognition based on the fused features, and finally it is determined whether the identity recognition for the user to be recognized is successful, if the identity recognition is successful, the user is further determined as the standard user with corresponding identity.

Specifically, the present disclosure further provides an mmWave radar-based non-contact identity recognition system, which is characterized in high reliability, good robustness, low power, high precision, and great convenience. The principle of recognition is as follows: First, after the recognition system emits low-power mmWaves, the system detects the echo signal generated by the signal reflected from the human body (such as: chest cavity, etc.), and extracts and reconstructs the heartbeat signal from the echo signal. Secondly, the reconstructed signal is matched with the heartbeat signal already entered in the database to realize identity recognition.

To sum up, the purpose of the present disclosure is to provide a non-contact identity recognition system and method, which are characterized in high reliability, good robustness, low power, high precision, and great convenience. The system includes: (1) an mmWave transceiver module; (2) a real-time signal processing module; (3) an identity recognition module.

In the system, the (1) mmWave transceiver module is specifically configured to: transmit mmWaves and receive mmWave echo signals, and the operation includes three parts: mmWave radar transceiving, high-precision A/D conversion, digital signal processing. The mmWave radar transceiving operation adopts MIMO antenna technology, which is composed of parallel microstrip antennas. Each transmitting antenna Tx has independent phase and amplitude control, and is able to transmit 77 GHz to 81 GHz chirp; while the receiving antennas Rx are able to work individually or together. The high-precision A/D conversion operation performs 16-bit high-precision analog-to-digital conversion on the signal received by the receiving antenna Rx. The digital signal processing operation adopts FPGA or DSP to preprocess the echo signal.

In the system, the (2) signal processing module is specifically configured to: extract and reconstruct the heartbeat signal from the mmWave echo signal. First, a UDP data packet is captured and returned in real time, and new data is spliced and packaged periodically. Second, the data is preprocessed, clutter interference is suppressed and echo selection is performed. Third, a bandpass filtering operation and iterative fitting are performed to extract the heartbeat signal.

In the system, the (3) identity recognition module is specifically configured to: first, extract features, and the operation includes performing beat separation and extracting the features of each beat signal; secondly, select features, and the operation includes screening out features that are more relevant to identity; thirdly, perform classification algorithm, and the operation includes training the classification model on the training set, verifying the recognition accuracy of the model on the testing set, and then identifying the target identity on the basis of the fusion of single-beat prediction results.

Figure 2:
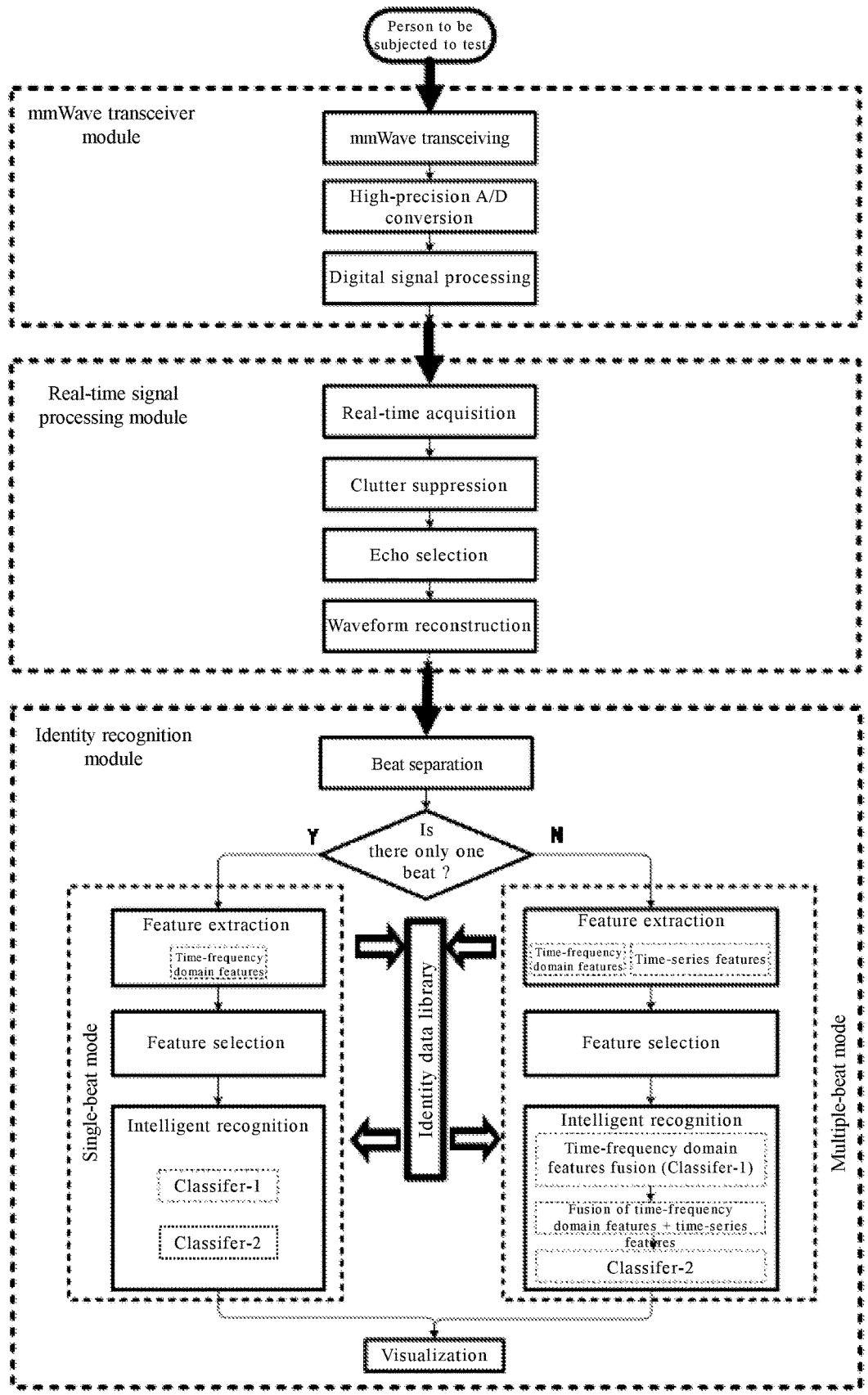
FIG. 2 is a block diagram of an mmWave radar-based non-contact identity recognition system provided by an embodiment of the present disclosure.

In a specific example, the present disclosure is an mmWave radar-based non-contact identity recognition system, the block diagram of which is shown in FIG. 2, and the system mainly includes:

(1) An mmWave transceiver module performs mmWave transceiving operation, high-precision A/D conversion and digital signal processing operation. The mmWave transceiver module adopts frequency modulated continuous wave (FMCW) mmWave radar, which includes two transmitting antennas Tx and four receive antennas Rx. Specifically, the transmitting end generates a chirp signal, and after the chirp signal passes through the power amplifier, the transmitting antenna sends a sawtooth wave with Chirp period of $T_f$ and a frequency modulation bandwidth of B, and a frame period thereof (that is, the sawtooth wave repetition period, each frame period contains multiple Chirps) is $T_i$, as shown in FIG. 2. The receiving antenna at the receiving end receives and preprocesses the echo signals generated by reflections from various objects and human bodies in the environment. The echo signal is mixed with the original signal after passing through the low-noise amplifier, and the A/D conversion is performed after the mixed passes through the intermediate frequency amplifier to obtain a digital signal, and then the digital signal is processed by the main control unit in a high-precision DSP or FPGA sub-module.

(2) A real-time signal processing module performs real-time acquisition and processing of echo signals and extracts heartbeat signals, and the operation mainly includes four parts: real-time acquisition of echo signal, clutter suppression, echo selection, and waveform reconstruction. The specific process is as follows:

(2-1) Real-time acquisition. The UDP port is monitored through a Socket sub-module, and a UDP data packet is captured in real time and the raw data is saved in the host computer.

(2-2) Clutter suppression. The echo signal of the mmWave may include various clutter interferences, including: stationary noise that is reflected from static objects (such as tables and walls), non-stationary noise that is reflected from moving objects, etc. Clutter is prone to aliasing and causing great interference to heartbeat signal monitoring. The disclosure adopts self-adaptive background subtraction and singular value decomposition to filter out stationary noise and non-stationary noise, respectively.

Figure 3:
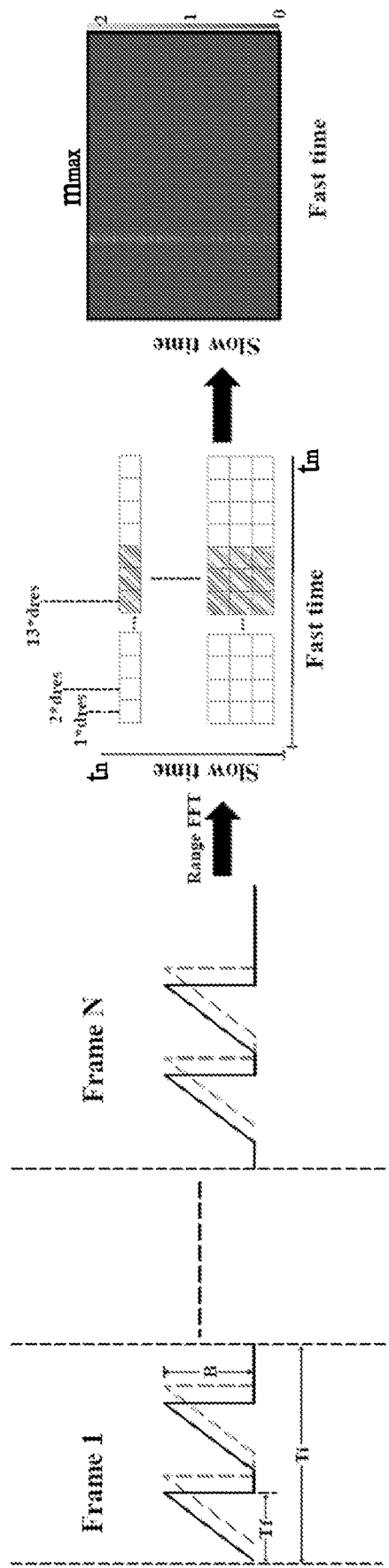
FIG. 3 is a principle diagram of acquiring echo signals by the mmWave radar provided by an embodiment of the present disclosure.

(2-3) Echo selection. The distance of the target to be recognized is accurately positioned, and a column of signals characterizing the distance unit are selected from the echo signal matrix, and the column of signals include the (original) signal related to the heart rate of the target to be recognized. First, Fourier transform is performed on each row of the echo signal Q to obtain an N×M range-time map matrix R, and N represents the number of Frames (i.e., frames), M represents the number of sampling points of each Chirp, as shown in the small figure on the left of FIG. 3; each column of the matrix R represents a distance unit, as shown in FIG. 3. For example: the distance unit characterized by the m-th column is m×$d_{res}$, and $d_{res}$ is the distance resolution of the mmWave radar. The distance resolution is $$d_{res} = \frac{c}{2B},$$

which may be flexibly adjusted by modifying the relevant parameters of the mmWave radar, and c is the speed of light, and B is the frequency modulation bandwidth of the sawtooth wave, as shown in FIG. 3. For example, if B=4 GHz, then $d_{res}$=3.76 cm. Next, the sum of energy on each distance unit is calculated, $E(m)=\Sigma_{n=1}^{N}|R_n(m)|^2$, m∈[1, M], as shown in the small figure in the middle of FIG. 3. Thirdly, the column where the maximum energy sum max (E(m)) is located is found, and the column index thereof is recorded as $m_{max}$. As shown in the small figure on the right of FIG. 3, the distance unit characterized by this column is the distance between the target to be recognized and the mmWave recognition system. Fourthly, the $m_{max}$-th column of signal is extracted from the matrix Q, and the arctangent function is adopted to calculate its phase and perform phase unwrapping operation, and the result is recorded as the sequence x(n), n∈[1, N].

(2-4) Waveform reconstruction. Bandpass filtering and iterative fitting are performed to extract the heartbeat signal. First, the discrete wavelet transform of the sequence x(n) is calculated, DWT{x(n)}. Secondly, bandpass filtering is performed in the wavelet domain, $\Sigma_{f_L}^{f_H}$ DWT{x(n)}, in which $f_L$=0.5 Hz, $f_H$=2.5 Hz. Thirdly, the inverse wavelet transform is calculated, IDWT{$\Sigma_{f_L}^{f_H}$ DWT{x(n)}}, thereby preliminarily realizing the reconstruction of the heartbeat signal. Finally, an iterative algorithm is adopted to fit the heartbeat signal, and the heartbeat (photoplethysmography, PPG) waveform is reconstructed.

(3) Identity recognition module. The present disclosure regards identity recognition as a multivariate classification problem. On the basis of beat separation, the disclosure utilizes time-frequency domain analysis and deep learning altogether to extract relevant features, and performs multiple classification of targets to be recognized through classification models. In order to improve recognition efficiency and recognition accuracy, the present disclosure adopts a hybrid architecture of "single-beat+multiple-beat" for identity recognition, as shown in FIG. 2. On the one hand, in the single-beat mode, in a relatively short period of time (that is, a single-beat, each beat is about 0.4~2 second) and with the assistance of time-frequency domain analysis to extract relevant features, an intelligent classification model is constructed on the basis of feature selection to realize identity recognition; on the other hand, in the multiple-beat mode and in a relatively long period of time (i.e., multiple-beats), time-frequency domain analysis and deep learning are utilized altogether to extract relevant features and construct identity recognition algorithm. An intelligent classification model is constructed on the basis of feature fusion and feature selection to further improve the accuracy of recognition.

Both single-beat mode and multiple-beat mode interact with the identity database. The data of the library is collected through mmWave radar for identity recognition. The heart rate data of each person in the library at least contains no less than 150 beat samples. The feature set constructed in the library includes the time-frequency features of each beat and the time-series features of multiple-beats. In order to verify the performance of the back-end classification algorithm, the feature set may be divided, into training set and testing set.

The identity recognition module of the present disclosure performs four operations: performing beat separation, feature extraction, intelligent identification and visualization, and the specific processing process is as follows:

(3-1) Beat separation. The heartbeat signal is segmented beat by beat. Conventional beat separation is performed mainly by using peak detection, and each beat contains a peak, but such method is highly susceptible to interference from random noise. The present disclosure improves the conventional method by checking the slope. Firstly, after inverting the signal (that is, turning the signal upside down by 180°), the peak value detection is adopted to identify the valleys, and the peak value and the peak-peak distance are both greater than a certain threshold; secondly, it is determined whether there is a valid peak between two valleys and whether the peak is a valid peak; the valid peak should meet the following two conditions simultaneously: (i) the peak value exceeds a certain threshold; (ii) there is a zero-crossing point (which is identified by zero-crossing detection) between two valleys. If the above conditions are met, the beat segmentation is performed according to the front and rear valleys; if the above conditions are not met, the beat segmentation is not performed. Finally, the segmented single-beat signal and the original continuous signal are normalized to facilitate subsequent signal processing operations.

Figure 4:
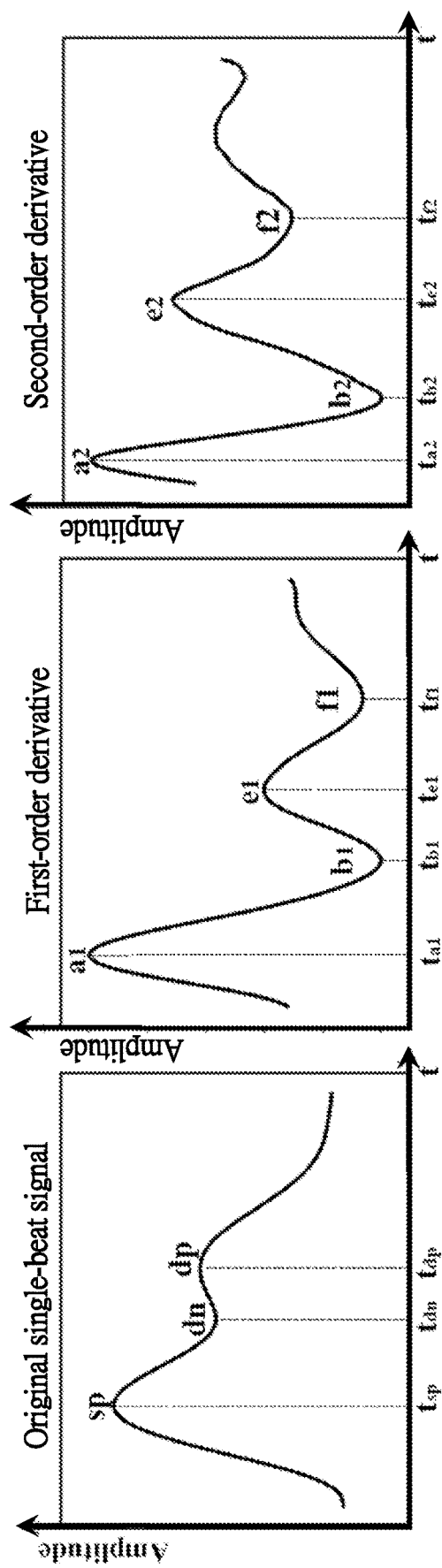
FIG. 4 is an explanatory diagram for extracting feature points corresponding to a single-beat provided by an embodiment of the present disclosure.

(3-2) Feature extraction. The specific operation process is as follows. First, it is determined whether the detected valid data contains only one beat, if so, the single-beat recognition mode is performed; if not, the multiple-beat recognition mode is performed as shown in FIG. 2. In the single-beat mode, the time-frequency domain features of a single-beat are extracted. In the multiple-beat mode, the time-frequency domain features of each beat are extracted separately, and then the features are input into CNN+BLSTM (convolutional neural network+bidirectional long short-term memory network) in a chronological order to further extract time-series features thereof. The features extracted by the present disclosure are shown in Table 1 and FIG. 4.

(3-2-1) Time-domain feature. The time-domain features of each beat are extracted through three dimensions, including feature point features, fiducial point features, and curve features. There are 46 types of time-domain features, including: 25 types of feature point features, 18 types of fiducial point features, and 3 types of curve features. First of all, with regard to the features of feature points, the features related to amplitude (such as: diastole and systole, etc.) are extracted from five aspects, including amplitude, time, area, slope and ratio. Secondly, with regard to the features of the fiducial point, relevant features are extracted from three aspects, including the first-order derivative, the second-order derivative and time thereof, for example: the amplitude ratio of the first valley of the second-order derivative to the first peak is b2/a2, which reflects the stiffness of the human artery and the expansion of peripheral arteries, and such feature varies from person to person. Thirdly, with regard to the features of curves, related features are extracted from three aspects, including curve width, fractal dimension value, and irregularity, among which curve width feature is the calculation of curve width features of beat at a certain height. In this embodiment, the width features of beat at 18 heights are extracted. For example, the pulse width is the width of the heartbeat signal having the half-maximum systolic peak value, and the width is related to the systemic vascular resistance of human body.

TABLE 1

List of beat features provided by the present embodiment

|  |  |  | Features | Explanation |
|---|---|---|---|---|
| Time domain features | Feature point features | Amplitude | Max, min, dn (dicrotic notch), max-min, mean, std, var, mad (mean absolute deviation), sp (systolic peak), dp (diastolic peak) | Maximum, minimum, dicrotic notch, difference between maximum and minimum, mean, standard deviation, variance, mean absolute deviation, systolic peak, diastolic peak |
|  |  | Time | $t_{sp}$, $t_{dp}$, $t_{dn}$, $\Delta t$, $t_{duration}$, $t_{rise}$, $t_{fall}$ | Systolic peak time, diastolic peak time, dicrotic notch time, time difference between systolic peak and diastolic peak, duration, rise time, fall time |
|  |  | Area | $A_{sp}$, $A_{dp}$, $A_{dp}/A_{sp}$ | Systolic area, diastolic area, diastolic to systolic area ratio |
|  |  | Slope | $Sl_{rise}$, $Sl_{fall}$ | Rising slope, falling slope |
|  |  | Ratio | dp/sp, (sp-dp)/sp, $t_{sp}$/sp | Augmentation index (i.e. the ratio of the diastolic peak amplitude to the systolic peak amplitude), relative augmentation index, systolic peak output curve |
|  | Fiducial point features | First-order derivative | $a_1$, $b_1$, $e_1$, $f_1$, $b_1/a_1$ | 1st peak, 1st valley, 2nd peak, 2nd valley of first-order derivative, and amplitude ratio of 1st valley of first-order derivative to 1st peak of first-order derivative |
|  |  | Second-order derivative | $a_2$, $b_2$, $e_2$, $f_2$, $b_2/a_2$ | 1st peak, 1st valley, 2nd peak, 2nd valley of second-order derivative, and amplitude ratio of 1st valley of second-order derivative to 1st peak of second-order derivative |
|  |  | Time | $t_{a1}$, $t_{b1}$, $t_{e1}$, $t_{f1}$, $t_{a2}$, $t_{b2}$, $t_{e2}$, $t_{f2}$ | The time corresponding to the fiducial point of the first-order and second-order derivatives |
|  | Curve features |  | cw (curve width), hfd (Higuchi fractal dimensions), irregularity | Curve width, Higuchi fractal dimension value, irregularity |
| Frequency domain features |  |  | $S_{mean}$, $S_{std}$, $S_{kurtosis}$, $S_{skewness}$, $S_{centroid}$, $C_{dwt}$, $C_{dct}$, $C_{mfc}$ (Mel frequency cepstral coefficients), $C_{dbt}$ (Daubechies wavelet transform coefficients) | Spectrum mean, standard deviation, kurtosis, skewness, centroid, discrete wavelet transform coefficients, discrete cosine transform coefficients, Mel frequency cepstral coefficients, Daubechies wavelet transform coefficients |
| Time-series features |  |  | CNN + BLSTM fully connected layer features | |

(3-2-2) Frequency-domain features. Frequency-domain features of each beat are extracted from 9 aspects, including mean, standard deviation, kurtosis, skewness, etc., and there are a total of 200 features.

(3-2-3) Time-series features. In this embodiment, the time-frequency domain features of each beat signal are sequentially input into the CNN+BLSTM model in chronological order, and the features of its fully connected layer are extracted to quantify the dynamic changes of heart rate. The CNN network is constructed using functions such as ConvID and Dense in the Python Keras library, while the BLSTM network is constructed using functions such as Bidirectional, LSTM and Dense in the Python Keras library. In this embodiment, a total of 178 time-series features are extracted.

(3-3) Feature selection. On the basis of feature preprocessing, redundant features are eliminated. First, exception feature handling and normalization operations are performed. Secondly, PCA (Principal Component Analysis) and correlation analysis are adopted altogether to screen out features that are highly correlated with identity classification labels.

(3-4) Intelligent recognition. Classification model is built based on XGBoost (Classifier-1 and Classifier-2, see FIG. 2), and the classifier is trained in the training set; the performance of the classifier is tested in the testing set, and the hyperparameters of the model are optimized by using grid search. The performance of the classifier is verified by ten-fold cross-validation.

(3-4-1) Intelligent recognition of single-beat mode is relatively simple. All of the beat samples of each person are extracted one by one from the identity database, and classifier-1 is utilized for recognition, and the recognition result is a vector w, w [$p_1, p_2, \ldots, p_m$], in which $p_j$ represents the probability that the beat of the currently recognized object is the j-th person, $j \in [1, m]$, m indicates that there are m persons in the identity database.

(3-4-2) The intelligent recognition of multiple-beat mode is relatively complex, and it is necessary to construct a multi-element classifier based on the fusion of time-frequency domain features and time-series features.

(3-4-2-1) Fusion of time-frequency domain features. With regard to fusion of time-domain and frequency-domain features of multiple-beat signals: First, the recognition result of multiple-beat is a collection of multiple-beat results, that is, a matrix W of n×m dimensions, $$W = \begin{bmatrix} p_{11} & \cdots & p_{1m} \\ \vdots & p_{ij} & \vdots \\ p_{n1} & \cdots & p_{nm} \end{bmatrix},$$

$i \in [1, n], j \in [1, m]$, in which $p_{ij}$ represents the probability that the i-th beat of the currently recognized object is the j-th person. Then, the average function is utilized to fuse the classification results. That is: each column of the probability matrix W is averaged to get a vector $\overline{w}$, $\overline{w}=[\overline{p}_1, \overline{p}_2, \ldots, \overline{p}_m]$, $j \in [1, m]$, in which $\overline{p}_j$ indicates the average value of the probability that the multiple-beat recognition result of the currently recognized object is the j-th person. The maximum value in the vector $\overline{w}$ is set to True, and the rest are set to False to get the final identity recognition result. For example, if $\overline{p}_k$=True, it means that the preliminary recognition result of the current beat sample is the k-th person in the identity database.

(3-4-2-2) Fusion of time-frequency domain features and time-series features. Fusion of time-frequency domain features and time-series features of multiple-beat signals: $\overline{w}$ is fused with time-series features extracted by CNN+BLSTM.

(3-4-2-3) A multi-class classification model is constructed by using XGBoost (classifier-2, see FIG. 2), and the final recognition result is provided.

Figure 5:
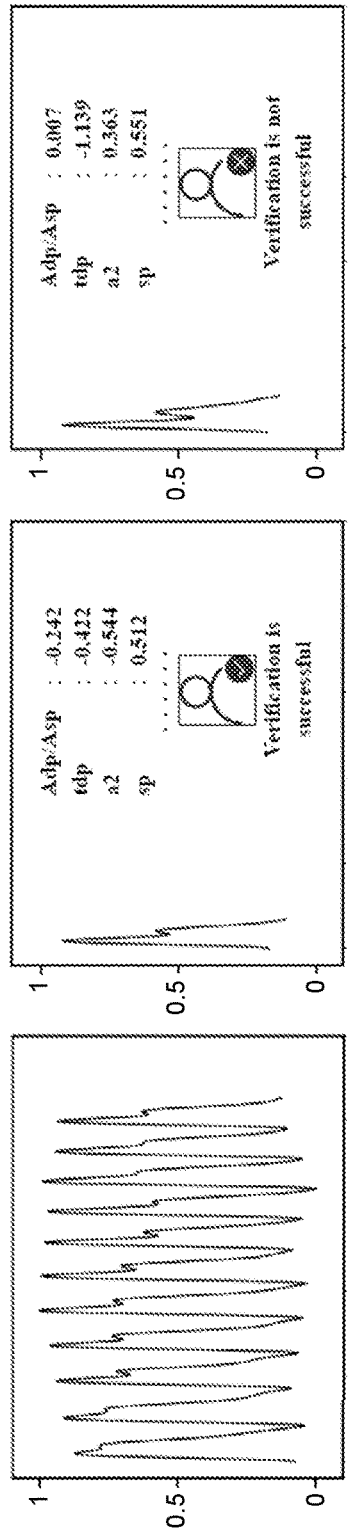
FIG. 5 is a diagram showing heartbeat signals of different objects under detection and a verification diagram showing extraction of single-beat signals provided by an embodiment of the present disclosure.
Figure 5:
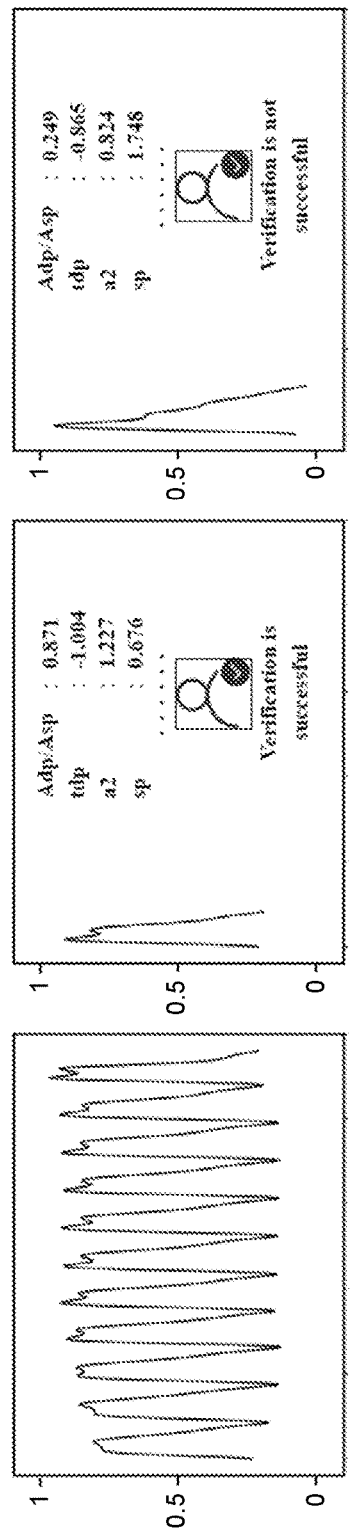

(3-5) Visualization. The recognition result is displayed visually, as shown in FIG. 5. In FIG. 5, the three small pictures arranged in parallel in (a) in the first row and (b) in the second row refer to the recognition result of two different users respectively. The picture on the left side shows the standard beat signal of the user, the picture in the middle is the visualization showing identity recognition for the user to be recognized is successful, and the picture on the right side is the visualization showing identity recognition for the user to be recognized is unsuccessful.

Figure 6:
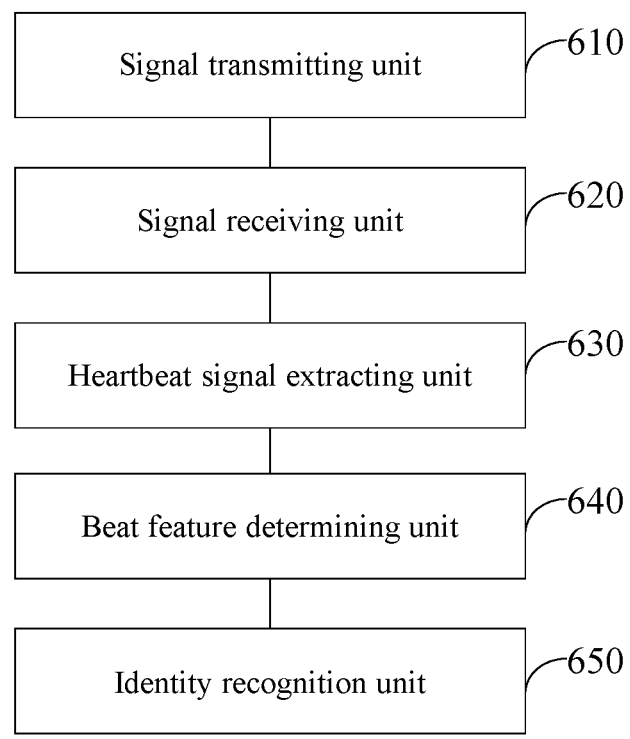
FIG. 6 is a schematic diagram of an mmWave radar-based non-contact identity recognition method provided by an embodiment of the present disclosure.

FIG. 6 is a schematic diagram of an mmWave radar-based non-contact identity recognition system provided by an embodiment of the present disclosure. As shown in FIG. 6, the system includes: a signal transmitting unit 610, a signal receiving unit 620, a heartbeat signal extracting unit 630, a beat feature determining unit 640, and an identity recognizing unit 650.

The signal transmitting unit 610 is configured to transmit an mmWave radar signal to the user to be recognized.

The signal receiving unit 620 is configured to receive an echo signal reflected from the user to be recognized.

The heartbeat signal extracting unit 630 is configured to perform clutter suppression and echo selection on the echo signal and extract the heartbeat signal of the user to be recognized.

The beat feature determining unit 640 is configured to segment the heartbeat signal of the user to be recognized beat by beat, and determine its corresponding beat features of the user to be recognized.

The identity recognizing unit 650 is configured to compare the beat features of the user to be recognized with the beat feature sets of the standard user group. If the beat features of the user to be recognized matches a beat feature set of one of the standard users in the standard user group, then the identity recognition for the user to be recognized is successful; otherwise, the identity recognition for the user to be recognized is not successful.

It can be understood that, for details on the functions of various units in FIG. 6, please refer to the description in the foregoing method embodiments, and details are not repeated here.

It is obvious for those skilled in the art that the above descriptions are only preferred embodiments of the present disclosure, and are not intended to limit the present disclosure. Any modifications, equivalent replacements and improvements made within the spirit and principles of the present disclosure should all be included within the protection scope of the present disclosure.

What is claimed is:

1. A millimeter-wave (mmWave) radar-based non-contact identity recognition method, comprising the following steps:
    transmitting an mmWave radar signal to a user to be recognized, and receiving an echo signal reflected from the user to be recognized;
    performing clutter suppression and echo selection on the echo signal, and then extracting a heartbeat signal of the user to be recognized;
    segmenting the heartbeat signal of the user to be recognized into a beat signal, wherein if only a single beat signal is contained after the segmentation, time-frequency domain features corresponding to the single beat signal are determined as beat features of the user to be recognized; if multiple-beat signals are contained after the segmentation, the time-frequency domain features of each of the beat signals are determined separately, and the time-frequency domain features are input into a neural network to extract its corresponding time-series features, so that the time-frequency domain features and the time-series features are used as the beat features of the user to be recognized, and determining its corresponding beat features of the user to be recognized; and comparing the features of the user to be recognized with beat features of a standard user group, wherein if the beat features of the user to be recognized matches a beat feature set of one of standard users in the standard user group, identity recognition for the user to be recognized is successful; otherwise, the identity recognition for the user to be recognized is not successful.

2. The mmWave radar-based non-contact identity recognition method according to claim 1, wherein performing the echo selection on the echo signal specifically comprises the following:

performing Fourier transform on each row of the echo signal to obtain a range-time map matrix of the mm Wave radar; calculating a sum of energy on a distance unit characterized by each column of the range-time map matrix, and selecting a maximum energy and a corresponding distance unit as a distance from an mmWave radar transmitting point to the user to be recognized, and extracting the maximum energy and the corresponding column in the range-time map matrix, utilizing an arctangent function to calculate a phase of each column and performing a phase unwrapping operation to obtain a signal related to a vital sign of the user to be recognized in the echo signal.

3. The mmWave radar-based non-contact identity recognition method according to claim 2, wherein extracting the heartbeat signal of the user to be recognized after performing the echo selection specifically comprises the following:

performing discrete wavelet transform on the signal subjected to the phase unwrapping operation, and performing bandpass filtering on the signal subjected to the discrete wavelet transform;

performing inverse wavelet transform on the signal subjected to the bandpass filtering to reconstruct the heartbeat signal of the user to be recognized.

4. The mmWave radar-based non-contact identity recognition method according to claim 3, wherein segmenting the heartbeat signal of the user to be recognized into the beat signal specifically comprises the following:

after turning the heartbeat signal of the user to be recognized upside down by 180°, utilizing peak detection to identify a valley, and a peak value and a peak-to-peak distance thereof are greater than a preset threshold; then turning the heartbeat signal back and determining whether there is a valid peak between two valleys; the valid peak needs to meet the following two conditions simultaneously: (i) the peak value exceeds a preset peak value threshold; (ii) there is a zero-crossing point (which is identified by zero-crossing detection) between the two valleys;

wherein if there is a valid peak, the beat segmentation is performed according to front and rear valleys; if there is no valid peak, the beat segmentation is not performed.

5. The mmWave radar-based non-contact identity recognition method according to claim 3, wherein segmenting the heartbeat signal of the user to be recognized into the beat signal specifically comprises the following:

after turning the heartbeat signal of the user to be recognized upside down by 180°, utilizing peak detection to identify a valley, and a peak value and a peak-to-peak distance thereof are greater than a preset threshold; then turning the heartbeat signal back and determining whether there is a valid peak between two valleys; the valid peak needs to meet the following two conditions simultaneously: (i) the peak value exceeds a preset peak value threshold; (ii) there is a zero-crossing point (which is identified by zero-crossing detection) between the two valleys;

wherein if there is a valid peak, the beat segmentation is performed according to front and rear valleys; if there is no valid peak, the beat segmentation is not performed.

6. The mmWave radar-based non-contact identity recognition method according to claim 1, wherein segmenting the heartbeat signal of the user to be recognized into the beat signal specifically comprises the following:

after turning the heartbeat signal of the user to be recognized upside down by 180°, utilizing peak detection to identify a valley, and a peak value and a peak-to-peak distance thereof are greater than a preset threshold; then turning the heartbeat signal back and determining whether there is a valid peak between two valleys; the valid peak needs to meet the following two conditions simultaneously: (i) the peak value exceeds a preset peak value threshold; (ii) there is a zero-crossing point (which is identified by zero-crossing detection) between the two valleys;

wherein if there is a valid peak, the beat segmentation is performed according to front and rear valleys; if there is no valid peak, the beat segmentation is not performed.

7. The mmWave radar-based non-contact identity recognition method according to claim 1, wherein comparing the beat features of the user to be recognized with the beat features of the standard user group specifically comprise the following:

if the heartbeat signal of the user to be recognized contains only the single beat signal after the segmentation, the beat features of the standard user group are extracted one by one, and a first classifier is utilized to identify the time-frequency domain features of the single beat signal of the user to be recognized, a recognition result is a vector w, w=$[p_1, p_2, \ldots, p_m]$, wherein an element $p_j$ in the vector w represents a probability that a beat of the user to be recognized is a j-th standard user in the standard user group, $j \in [1,m]$, m represents that there are m users in the standard user group; if a maximum value of elements in the vector w is greater than a preset probability threshold, the identity recognition for the user to be recognized is successful, and a user's identity is determined to be a standard user corresponding to the maximum value of the elements in the vector w;

if the heartbeat signal of the user to be recognized contains the multiple-beat signals after the segmentation, the beat features of the standard user group are extracted one by one, first of all, the first classifier is utilized to identify the time-frequency domain features of the multiple-beat signals of the user to be recognized, a recognition result is a matrix W of n×m dimensions, $$W = \begin{bmatrix} p_{11} & \cdots & p_{1m} \\ \vdots & p_{ij} & \vdots \\ p_{n1} & \cdots & p_{nm} \end{bmatrix},$$

$i \in [1, n], j \in [1,m]$, n represents that the user to be recognized contains n beats after the segmentation, m represents that there are m users in the standard user group, wherein an element $p_{ij}$ in the matrix w represents a probability that a i-th beat of the user to be recognized is the j-th standard user in the standard user group, an average function is adopted to average each column of the probability matrix W to obtain a vector $\overline{w}$, $\overline{w}=[\overline{p}_1, \overline{p}_2, \ldots \overline{p}_m]$, $j \in [1, m]$; wherein an element $\overline{p}_j$ in the vector $\overline{w}$ represents an average probability that the multiple-beat recognition result of the user to be recognized is the j-th standard user in the standard user group; if a maximum value of elements in the vector $\overline{w}$ is greater than the preset probability threshold, it is preliminarily determined that the user's identity is the standard user corresponding to the maximum value of the elements in the vector $\overline{w}$; next, the vector $\overline{w}$ identified by the first classifier is fused with a time-series domain features of the multiple beat signals of the user to be recognized, a second classifier is adopted to perform identity recognition based on the fused features, and finally it is determined whether the identity recognition for the user to be recognized is successful, if the identity recognition is successful, the user is further determined as the standard user with a corresponding identity.

\* \* \* \* \*